United States Patent

Huszár et al.

[11] Patent Number: 6,162,923
[45] Date of Patent: Dec. 19, 2000

[54] PROCESS FOR THE PREPARATION OF IMIDAZOLONES

[75] Inventors: Csaba Huszár; Attila Kis-Tamás, both of Budapest; Attila Németh, Göd; Antal Gajáry; Lajosné Páli, both of Budapest, all of Hungary

[73] Assignee: Sanofi-Synthelabo, Paris, France

[21] Appl. No.: 09/463,433

[22] PCT Filed: Jul. 22, 1998

[86] PCT No.: PCT/HU98/00065

§ 371 Date: Apr. 26, 2000

§ 102(e) Date: Apr. 26, 2000

[87] PCT Pub. No.: WO99/05118

PCT Pub. Date: Feb. 4, 1999

[30] Foreign Application Priority Data

Jul. 25, 1997 [HU] Hungary ................................. 9701296

[51] Int. Cl.[7] .................................................. C07D 235/02
[52] U.S. Cl. ........................................ 548/300.7; 564/189
[58] Field of Search ......................... 564/189; 548/300.7

[56] References Cited

U.S. PATENT DOCUMENTS 5,270,317 12/1993 Bernhart et al. ....................... 514/269

OTHER PUBLICATIONS

Bernhart et al., Journal of Medicinal Chemistry, vol. 36, No. 22, (1993), pp. 3371–3380.
Schollkopf et al., Liebigs Ann. Chem. No. 3, (1981), pp. 439–458.
Brunken et al., Chem. Ber., vol. 89, No. 6, Feb. 2, (1956), pp. 1363–1373.
Khokhlov et al., Journal of Medicinal Chemistry, vol. 54, No. 12, (1984), pp. 2414–2415.
Martinez et al., Journal of Molecular Structure, vol. 75, No. 2, (1981). pp. 241–254.
Schipper et al., Journal of American Chemical Society, vol. 74, (1952), pp. 350–353.
Houben–Weyl, Band VI/3, (1965), pp. 315–317.
Roberts et al., Journal of American Society, vol. 78, (1956), pp. 4778–4781
McElvain et al., Journal of American Chemical Society, vol. 68, (1946), pp. 1922–1925.

Primary Examiner—Laura L. Stockton
Attorney, Agent, or Firm—Birch, Stewart, Kolasch & Birch, LLP

[57] ABSTRACT

The present invention relates to a process for the preparation of a compound of general formula (I),

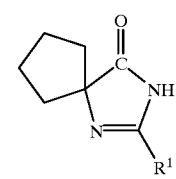

(I)

wherein $R^1$ represents a hydrogen atom or an alkyl group of 1–6 carbon atoms, and their salts, wherein the compound of formula (II):

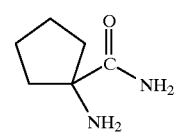

(II)

is reacted with a compound of formula (III):

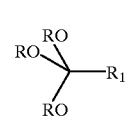

(III)

wherein R represents an alkyl group of 1–4 carbon atoms and $R^1$ is the same as defined above, by heating their neutral pH mixtures at the boiling temperature of the mixture, and the resulting compound of general formula (IV):

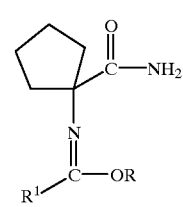

(IV)

wherein R and $R^1$ are the same as defined above, is cyclized into the compound of general formula (I) by further elevating the temperature of the neutral mixture, and if desired, the compounds of general formula (I) are transformed into their salts, or the compounds of general formula (I) are liberated from their salts.

6 Claims, 1 Drawing Sheet

(I)
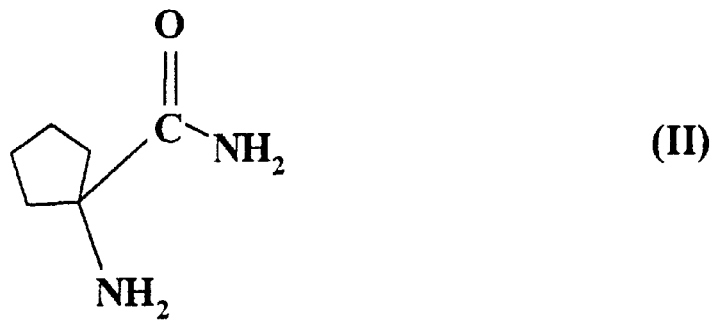
(II)
(III)
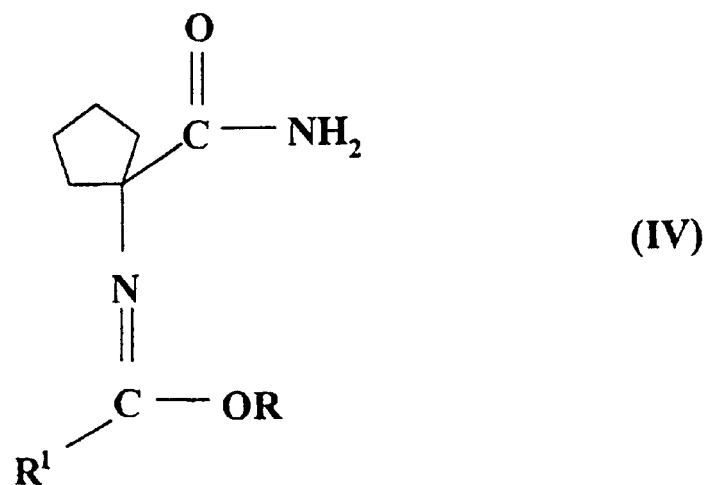
(IV)

PROCESS FOR THE PREPARATION OF IMIDAZOLONES

This application is the national phase under 35 U.S.C. §371 of PCT International Application No. PCT/HU98/00065 which has an International filing data of Jul. 22, 1998, which designated the United States of America.

This invention relates to the new process for the preparation of compounds of general formula (I)—wherein $R^1$ means hydrogen atom or alkyl group of 1–6 carbon atoms—, and to the compounds of general formula (IV)—wherein R means hydrogen atom or alkyl group of 1–4 carbon atoms and $R^1$ is the same as defined above.

Compounds of general formula (I) are intermediates of compounds with angiotensin-II antagonist activity which are described in Hungarian Patent, No. 211.839 and in the equivalent U.S. Pat. No. 5,270,317.

The above patents, among others, describe a hypotetic reaction route, "reaction scheme B", by this route compounds of general formula (I) might be synthetised from amino-acylamides and ortho esters in acidic medium. In the above specifications this hypothetic reaction route is not demonstrated by examples.

For one skilled in the art, in the knowledge of the prior, this hypothetic reaction route, which applies acidic medium, does not seem to be feasible, since it is known that ortho esters suffer decomposition on the effect of acids/Houben-Weyl Band VI/3 S 315 (1965)/. It is well-known, too, that the lone-pair of electron of primary amines in acidic medium is not available for further reactions, as it takes part in the salt formation. It is also known, that in acidic medium primary amines and ortho esters also give rise to N-aryl-N-alkylformamides, from which the compounds of general formula (I) may not be formed/J. Am. Chem. Soc. 78 p 4778 (1956)/.

BRIEF DESCRIPTION OF DRAWINGS

FIG. 1 describes the imidazolone products of formula (I), the reactants of formulas (II) and (III) and the intermediates of formula (IV).

In the knowledge of the above we aimed to find a process for the preparation of compounds of general formula (I) which proceeds in good yield and results pure product. We found that if the compound of formula (II) is reacted with a compound of general formula (III)—wherein R means an alkyl group of 1–4 carbon atoms and $R^1$ is the same as defined above—, by heating their neutral mixtures at reflux temperature, and the resulting compound of general formula (IV)—wherein R and $R^1$ are the same as defined above—, is cyclized into the compound of general formula (I) by further elevating the temperature of the neutral pH mixture, and if desired, the compound of general formula (I) is transformed into its salt, or the compound of general formula (I) is liberated from its salt, then the compounds of general formula (I) are obtained in very pure condition, in almost theoretical yields, even applying just equivalent amounts of reactants.

Our invention furthermore relates to the new compounds of general formula (IV) which are useful intermediates in the process described above.

According to a preferred embodiment of the invention the compound of formula (II) is mixed with a compound of general formula (III), the reaction is carried out at the boiling point of the mixture, the resulting compound of general formula (IV), optionally without isolation, is then cyclized by enhancing the temperature of the reaction mixture to 110–160° C., in neutral reaction medium, under conditions of distillation or vacuum distillation. When the reaction mixture containing the resulting compounds of general formula (I) is acidified, the compounds compounds of general formula (I) are obtained in the form of their acid addition salt.

The compound of formula (II) can be synthetised as described in the above two patents in Examples 2a and 2b, whereas the compounds of general formula (III) can be prepared according to J. Am. Chem. Soc. 68 p 1923 (1946).

Further details of our process are illustrated by the following examples, without limiting our claims to the content of examples.

EXAMPLE 1

2-butyl-1,3-diaza-spiro[4,4]non-1-en-4-one-monohydrochloride 20 g (0.156 mol) of 1-aminocyclopentane-1-carboxamide and 31 g (0.19 mol) of trimethyl orthovalerate are refluxed at 70–80° C. inner temperature for 1 hour. The condenser is then changed to a "No hold up" condenser, while heating and stirring are continued to distille off volatile components. The reaction is completed in vacuo. The residue is dissolved in 150 ml of acetone the pH is adjusted to 1–2, after cooling the resulting suspension the product is filtered off.

31 g of the title compound is obtained, yield 86.4%.

IR: 3600–2200: vibr, NH; 1779: γc=o; 1642 γc, 1517: δNH (IRFT Perkin Elmer)

1H NMR: 0.9 ppm T ($CH_3$); 1.34 ppm S ($CH_2$); 1.73 ppm Q ($CH_2$); 1.78–2.01 ppm M cyclopentane ($CH_2$); 2.78 ppm T ($CH_2$); 9–15 ppm (NH, N)

MS: 194, 179, 166, 165, 152, 124, 84, 83, 54, 41

TLC: eluent chloroform: methanol=6:1, TLC plate Kieselgel GF254.

Detection: $I_2$ vapors Rf=0.64

EXAMPLE 2

1,3-diazaspiro[4,4]non-1-en-4-one monohydrochloride 20 g (0.156 mol) of 1-aminocyclopentane-1-carboxamide and 28 g (0.19 mol) of trimethyl orthoformate are refluxed for 1 hour. The condenser is then changed to a "No hold up" condenser, and the temperature is elevated to 140° C. inner temperature. The residue is dissolved in 150 ml of acetone the pH is adjusted to 1–2 with concentrated hydrochloric acid and after cooling the resulting suspension the product is filtered of. 25 g of the title compound is obtained, yield 92.2%.

Mp: 219–221° C. (decomp.)

IR: 1663 $cm^{-1}$ C=N 1739 $cm^{-1}$ C=O 3197 $cm^{-1}$ H(NH)

$MH^+$: 139

EXAMPLE 3

N-(1-carboxamidocyclopentyl-1)formimino ethyl ether 12.8 g (0.1 mol) 1-amino-1-carboxamidocyclopentane and 15 g (0.101 mol) of triethyl orthoformate was heated at 80° C. for 1 hour. Volatile materials formed in the reaction were distilled off in fine vacuum. The residual 18 g (97.8%) of oily material was identified by IR and MS as the title compound.

IR: 1650 cm$^{-1}$: CO(CONH) 1625 cm$^{-1}$: C=N 3350 cm$^{-1}$: H(amide)

MH$^+$: 185

EXAMPLE 4

N-(1-carboxamidocyclopentyl-1)pentaneimino methyl ether 12.8 g (0.1 mol) of 1-amino-1-carboxamidocyclopentane and 16.2 g (0.1 mol) of trimehyl orthovalerate was stirred at 80° C. for 1 hour. Volatile materials formed in the reaction were distilled off in fine vacuum. The residual 22.6 g (99%) of oily material was identified by IR and MS as the title compound.

IR: 1650 cm$^{-1}$: CO(CONH) 1630 cm$^{-1}$: C=N 3297 cm$^{-1}$: H(amide)

MH$^+$: 227

What is claimed is:

1. A process for the preparation of a compound of general formula (I):

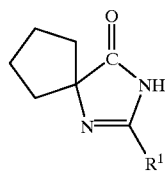
(I)

wherein R$^1$ represents a hydrogen atom or an alkyl group of 1–6 carbon atoms, and their salts, wherein the compound of formula (II):

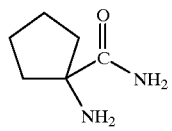
(II)

is reacted with a compound of formula (III):

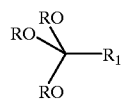
(III)

wherein R represents an alkyl group of 1–4 carbon atoms and R$^1$ is the same as defined above, by heating their neutral pH mixtures at the boiling temperature of the mixture, and the resulting compound of general formula (IV):

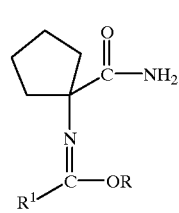
(IV)

wherein R and R$^1$ are the same as defined above, is cyclized into the compound of general formula (I) by further elevating the temperature of the neutral mixture, and if desired, the compounds of general formula (I) are transformed into their salts, or the compounds of general formula (I) are liberated from their salts.

2. The process as defined in claim 1, wherein the reaction of the compound of formula (II) with the compound of general formula (III), where R is a methyl group, and R$^1$ is n-butyl group, is carried out by heating at 70–80° C. under reflux conditions.

3. The process as defined in claim 1, wherein the resulting compound of general formula (I) is transformed in the reaction mixture into its hydrochloride salt and isolated in the form of this salt.

4. A compound of general formula (IV):

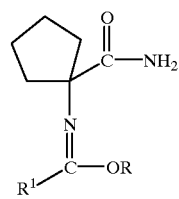
(IV)

wherein R is an alkyl group of 1–4 carbon atoms and R$^1$ is a hydrogen atom or an alkyl group of 1–6 carbon atoms.

5. N-(1-carboxamidocyclopentyl-1)-formimino ethyl ether.

6. N-(1-carboxamidocyclopentyl-1)-pentanimino methyl ether.

* * * * *